(12) United States Patent
Jan et al.

(10) Patent No.: US 10,317,370 B2
(45) Date of Patent: Jun. 11, 2019

(54) METHOD FOR ACQUIRING DYNAMIC VIBRATION FREQUENCY

(71) Applicant: METAL INDUSTRIES RESEARCH & DEVELOPMENT CENTRE, Kaohsiung (TW)

(72) Inventors: Chia-Ming Jan, Kaohsiung (TW); Wen-Chieh Wu, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 309 days.

(21) Appl. No.: 15/279,715

(22) Filed: Sep. 29, 2016

(65) Prior Publication Data

US 2017/0168023 A1 Jun. 15, 2017

(30) Foreign Application Priority Data

Dec. 9, 2015 (TW) .............................. 104141263 A

(51) Int. Cl.
*G01H 1/00* (2006.01)
*G01N 29/44* (2006.01)
*G01N 29/12* (2006.01)

(52) U.S. Cl.
CPC ............. *G01N 29/12* (2013.01); *G01H 1/003* (2013.01); *G01H 1/006* (2013.01); *G01N 29/4463* (2013.01); *G01N 2291/014* (2013.01); *G01N 2291/105* (2013.01)

(58) Field of Classification Search
CPC ............... G01N 29/12; G01N 29/4463; G01N 2291/014; G01N 2291/105; G01H 1/003; G01H 1/006

USPC .................................. 73/579, 659, 660, 661
See application file for complete search history.

(56) References Cited

U.S. PATENT DOCUMENTS

| | | | | |
|---|---|---|---|---|
| 3,610,029 A | * | 10/1971 | Carlson | .................... G01H 1/10 336/130 |
| 5,243,279 A | * | 9/1993 | Bajat | ...................... G01D 5/147 310/68 B |
| 2009/0133529 A1 | * | 5/2009 | Kister | ................... F16F 15/162 74/573.11 |
| 2014/0027216 A1 | * | 1/2014 | Ohara | ..................... C23C 2/003 188/267 |
| 2014/0067289 A1 | | 3/2014 | Baldwin | |

* cited by examiner

*Primary Examiner* — Justin Seo
*Assistant Examiner* — Rose M Miller
(74) *Attorney, Agent, or Firm* — Juan Carlos A. Marquez; Marquez IP Law Office, PLLC

(57) ABSTRACT

A method for acquiring a dynamic vibration frequency includes the following steps. At least five pairs of vibration measurement elements are selected. A bandwidth range of the vibration measurement elements is determined. The vibration measurement elements in sequence on a first side and a second side, which are geometrically symmetrical to each other, of a main shaft are used to measure vibration displacements in a symmetrical position arranging manner. The vibration displacements measured by the vibration measurement elements of either of the first side and second side are corrected, so as to differentially eliminate an ambient noise. Positions of nodes located on the first side and the second side are calculated. The vibration displacements in the preceding steps are used to deduce dynamic vibration frequencies of main harmonics. A vibration mode of the main shaft is confirmed.

9 Claims, 4 Drawing Sheets

METHOD FOR ACQUIRING DYNAMIC VIBRATION FREQUENCY

CROSS-REFERENCE TO RELATED APPLICATION

This application claims the benefit of Taiwan Patent Application No. 104141263, filed on Dec. 9, 2015, which is hereby incorporated by reference for all purposes as if fully set forth herein.

TECHNICAL FIELD

The present disclosure relates to a method for acquiring a dynamic vibration frequency, and in particularly, to a method for acquiring a dynamic vibration frequency during machining.

BACKGROUND

Remands in the micro-milling process machining market surge, and the competition focus of the industry has been developed toward intelligentization, wherein the most important section is real-time machining vibration monitoring and consideration, which may serve as main shaft running status understanding and device process yield control. However, currently, a commercially available machining vibration sensing apparatus with high precision has a relatively high unit price and unfavorable introduction feasibility.

A main function of on-line chatter avoidance is protecting a cutting machine tool. By means of a mini-sized vibration sensing element mounted in a machining area of the cutting machine tool (for example, on sheet metal of a main shaft), analysis software disposed on a rear end can detect a dynamic vibration frequency during single machining, but lacks of a cutting vibration mode information. If the dynamic vibration frequency and the vibration mode information of machining of the main shaft are both known, a status of the machining may be adjusted, and a rotation speed and feeding of the main shaft can be changed on line, so as to minimize waste of a workpiece material and also prevent a cutting tool from being damaged.

The U.S. Patent Publication No. US 20140067289A1 discloses an integrated vibration measurement and analysis system, which includes a vibration measurement signal processing method, an integration or differentiation vibration signal may be analyzed in real time by using a filter means of an IIR, so as to lower a complex degree of system hardware and a data storage demand.

However, the foregoing patent document does not disclose a method to directly eliminate an ambient noise and quickly obtain dynamic vibration frequency and mode information during machining.

In view of this, therefore, it is necessary to provide a method for acquiring a dynamic vibration frequency and a vibration mode on line to resolve the foregoing problems.

SUMMARY

In view of this, therefore, a main objective of the present disclosure is to provide a method for acquiring a dynamic vibration frequency, which can directly eliminate an ambient noise and quickly obtain a dynamic vibration frequency and a vibration mode during machining.

To achieve the above objective, the present disclosure provides a method for acquiring a dynamic vibration frequency, comprising the following steps of: selecting at least five pairs of vibration measurement elements, which comprise a first pair of vibration measurement elements to a fifth pair of vibration measurement elements, wherein the first pair of vibration measurement element comprises two first vibration measurement elements, the second pair of vibration measurement element comprises two second vibration measurement elements, and so forth; determining a bandwidth range of the first pair of vibration measurement elements to the fifth pair of vibration measurement elements; using the first pair of vibration measurement elements to the fifth pair of vibration measurement elements in sequence on a first side and a second side, which are geometrically symmetrical to each other, of a main shaft to measure vibration displacements in a symmetrical position arranging manner; correcting the vibration displacements measured by the first vibration measurement element to the fifth vibration measurement element of either of the first side and second side by using a vibration displacement difference measured between the first pair of vibration measurement elements, between the third pair of vibration measurement elements, or between the fifth pair of vibration measurement elements, so as to differentially eliminate an ambient noise; performing interpolation calculation on the corrected and uncorrected vibration displacements of the first pair of vibration measurement elements, the third pair of vibration measurement elements, and the fifth pair of vibration measurement elements by using the corrected and uncorrected vibration displacements of the second pair of vibration measurement elements and the fourth pair of vibration measurement elements, so as to calculate positions of at least one pair of nodes located on the first side and the second side; using the vibration displacements in the preceding steps to deduce dynamic vibration frequencies of one pair of main harmonics; and confirming a vibration mode of the main shaft.

In the design of the present disclosure, a dynamic vibration frequency in a cutting process may be quickly measured by using a symmetrical position arranging manner of multiple vibration measurement elements. Because sensed signals of symmetrically arranged positions have the same theoretical value, but are affected by the environment to different extents. Thus, a dynamic vibration frequency, a mode, and a node position during machining may be clearly learned by means of a signal difference calculation manner. The technology of the present disclosure can prevent the precision of the measurement system from being affected by ambient interference, so that a dynamic vibration frequency and a vibration mode during machining may be accurately acquired.

In order to make the foregoing and other objectives, features, and advantages of the present disclosure more obvious, the present disclosure is described in detail below by referring to the accompany drawings.

DETAILED DESCRIPTION OF DISCLOSED EMBODIMENTS

Figure 1:
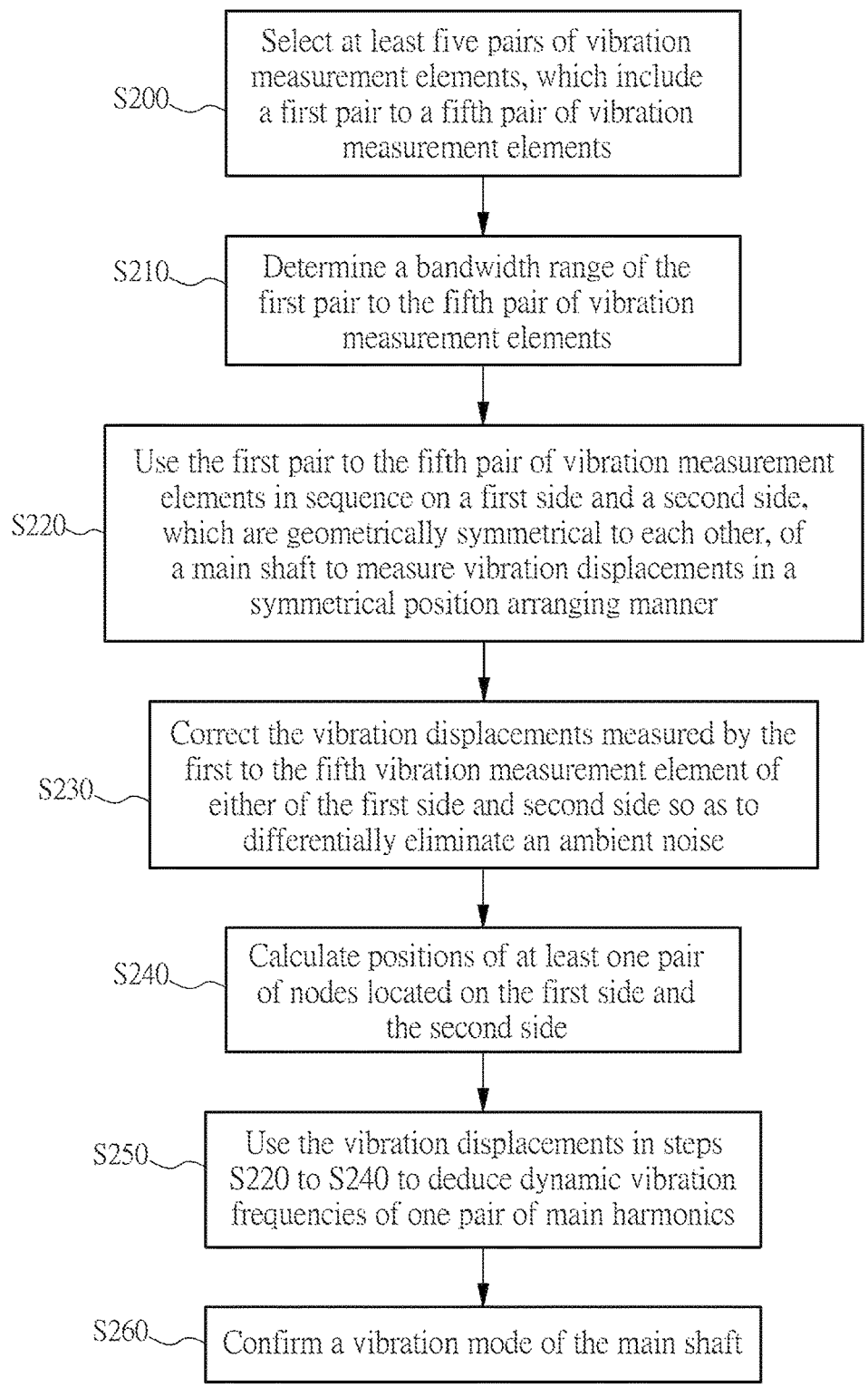
FIG. 1 is a flowchart of a method for acquiring a dynamic vibration frequency according to an embodiment of the present disclosure.
Figure 2A:
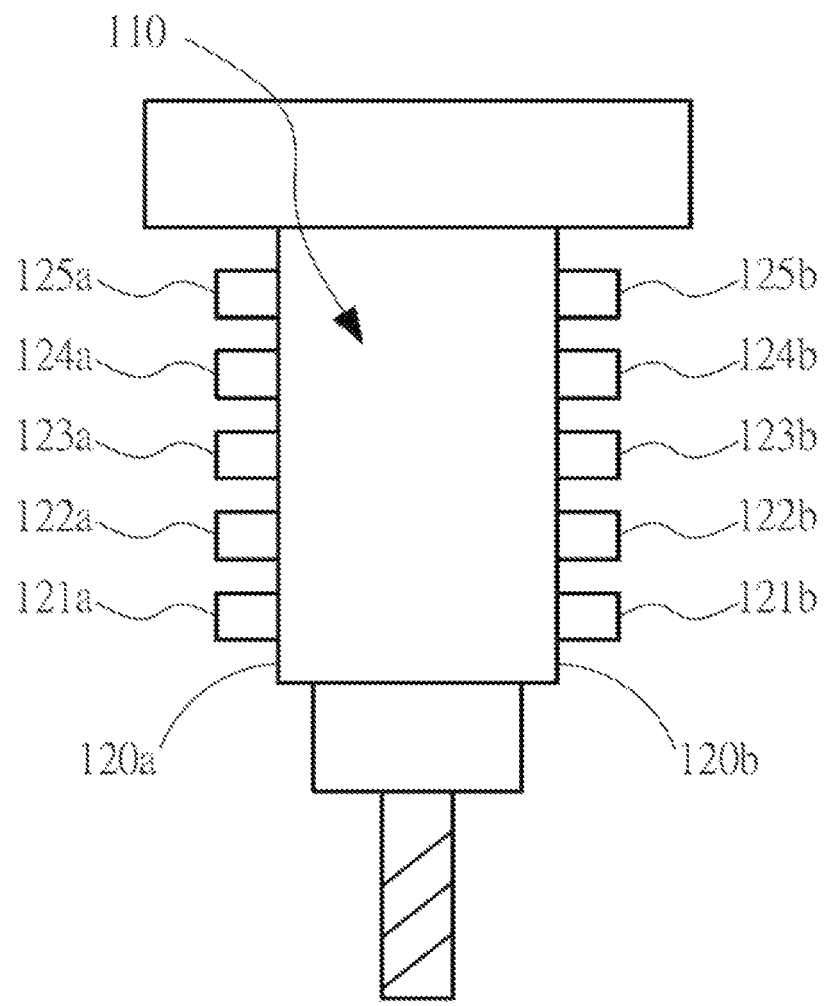
FIG. 2a is a side view of at least five pairs of vibration measurement elements according to an embodiment of the present disclosure.
Figure 2B:
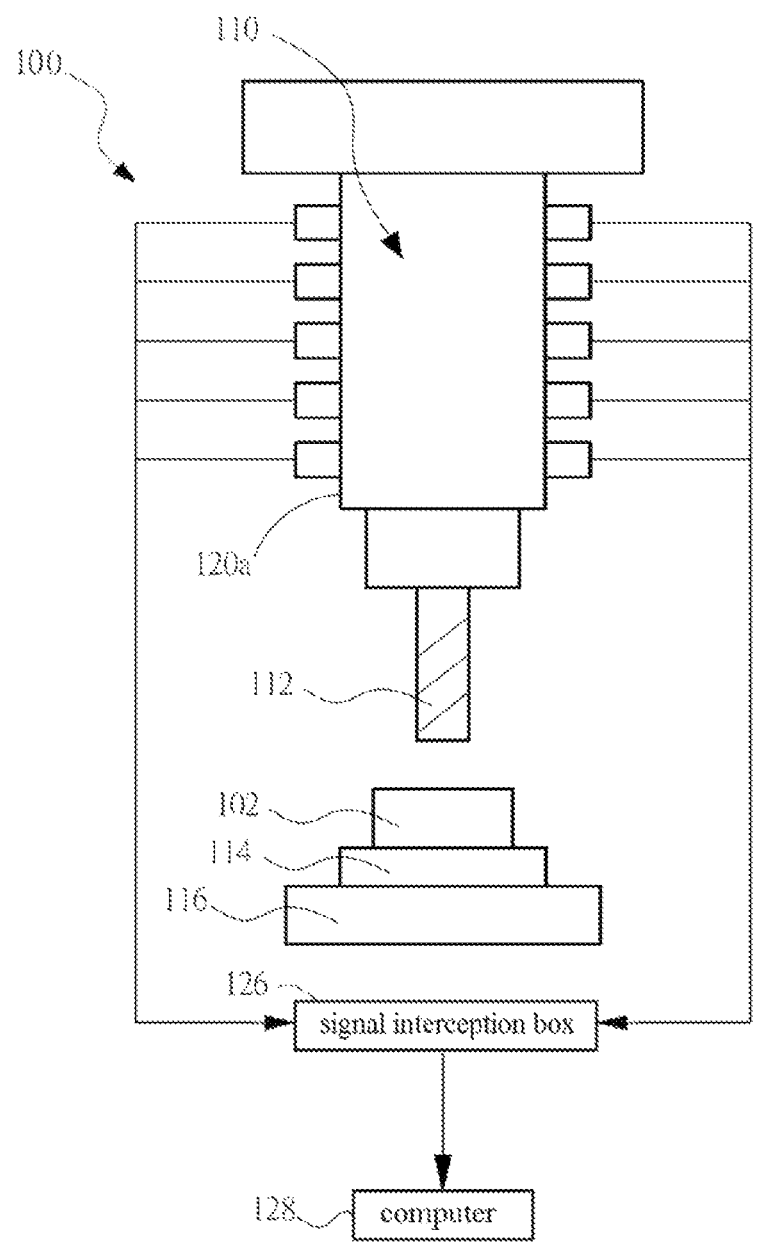
FIG. 2b is a side view of a cutting machine tool and a measurement system according to an embodiment of the present disclosure.

Refer to FIG. 1, which shows a method for acquiring a dynamic vibration frequency according to an embodiment of the present disclosure, including the following steps:

Step S200: Select at least five pairs of vibration measurement elements, which include a first pair of vibration measurement elements to a fifth pair of vibration measurement elements. Refer to FIG. 2a, which shows the first pair of vibration measurement elements to the fifth pair of vibration measurement elements according to an embodiment of the present disclosure. The first pair of vibration measurement elements 121a, 121b includes two first vibration measurement elements 121a, 121b, the second pair of vibration measurement elements 122a, 122b includes two second vibration measurement elements 122a, 122b, and so forth. The vibration measurement element may be a vibration accelerometer, configured to measure a vibration displacement. Refer to FIG. 2a and FIG. 2b, a measurement system includes the first pair to the fifth pair of vibration measurement elements, namely, ten vibration measurement elements 121a, 121b, 122a, 122b, 123a, 123b, 124a, 124b, 125a, 125b, in total, a signal interception box 126, and a computer 128, wherein the first pair to the fifth pair of vibration measurement elements 121a, 121b, 122a, 122b, 123a, 123b, 124a, 124b, 125a, 125b are electrically connected to the signal interception box 126, and the signal interception box 126 is electrically connected to the computer 128.

Step S210: Determine a bandwidth range of the first pair to the fifth pair of vibration measurement elements. For example, a bandwidth range of the first pair to the fifth pair of vibration measurement elements 121a, 121b, 122a, 122b, 123a, 123b, 124a, 124b, 125a, 125b, is determined to be 50 Hz to 10 KHz. The bandwidth range of the first pair to the fifth pair of vibration measurement elements 121a, 121b, 122a, 122b, 123a, 123b, 124a, 124b, 125a, 125b shall cover an operating frequency range of a main shaft (for example, 150 Hz to 400 Hz).

Step S220: Use the first pair to the fifth pair of vibration measurement elements in sequence on a first side and a second side, which are geometrically symmetrical to each other, of a main shaft to measure vibration displacements in a symmetrical position arranging manner. Further refer to FIG. 2b, the main shaft is a main shaft 110 of a cutting machine tool 100. In detail, the cutting machine tool 100 further includes a cutting tool 112, a fixture jig 114, and a machine tool platform 116. The cutting tool 112 is fixedly disposed on the main shaft 110 and is configured to cut a workpiece 102 in a rotating manner, the fixture jig 114 is configured to clamp the workpiece 102, and the machine tool platform 116 is configured to support and hold the fixture jig 114.

The first pair to the fifth pair of vibration measurement elements 121a, 121b, 122a, 122b, 123a, 123b, 124a, 124b, 125a, 125b are symmetrically fixedly disposed on a first side 120a and a second side 120b of the main shaft 110 in sequence. Positions of the first pair to the fifth pair of vibration measurement elements 121a, 121b, 122a, 122b, 123a, 123b, 124a, 124b, 125a, 125b on the first side 120a and the second side 120b of the main shaft 110 are geometrically symmetrical positions of the main shaft 110 (for example, symmetrical positions in terms of the shape of the main shaft). In this embodiment, two adjacent vibration measurement elements of the first to the fifth vibration measurement elements 121a, 122a, 123a, 124a, 125a on the first side 120a are distributed on the main shaft at a same distance, two adjacent vibration measurement elements of the first to the fifth vibration measurement elements 121b, 122b, 123b, 124b, 125b on the second side 120b are also distributed on the main shaft at a same distance, and e.g., a distance between the two adjacent vibration measurement elements is about 50 mm. In another embodiment, two adjacent vibration measurement elements of first to the fifth vibration measurement elements on the same side are distributed on the main shaft at different distances, and a distance between the two adjacent vibration measurement elements may be adjusted to another numerical value according to a design requirement.

Step S230: In a machining state, correct the vibration displacements measured by the first vibration measurement element to the fifth vibration measurement element of either of the first side and second side by using a vibration displacement difference measured between the first pair of vibration measurement elements, between the third pair of vibration measurement elements, or between the fifth pair of vibration measurement elements, so as to differentially eliminate an ambient noise (in brief, by means of analysis of comparison between two signals, the ambient noise is canceled by using a signal subtraction manner). Because the so-called symmetrical position arrangement refers to that the vibration measurement elements are arranged at geometrical corresponding positions on the main shaft 110, during vibration, the positions have vibration signals having the same gain. Elimination of an ambient noise may be accomplished by using the foregoing vibration signals having the same gain as a basic value and by using a signal difference calculation manner.

In this embodiment, the step of correcting the vibration displacements measured by the first to the fifth vibration measurement elements of either of the first side and second side includes the following step: calculating a first vibration displacement difference measured between the first pair of vibration measurement elements, a third vibration displacement difference measured between the third pair of vibration measurement elements, and a fifth vibration displacement difference measured between the fifth pair of vibration measurement elements, wherein the first, third, and fifth vibration displacement differences are regarded as interference values generated by at least one ambient noise. For example, refer to Table 1, which shows original vibration displacements measured by the first to the fifth vibration measurement elements 121a, 122a, 123a, 124a, 125a of the first side 120a and the first to the fifth vibration measurement elements 121b, 122b, 123b, 124b, 125b of the second side 120b. Refer to Table 2, which shows the first vibration displacement difference measured between the first pair of vibration measurement elements 121a, 121b, the third vibration displacement difference measured between the third pair of vibration measurement elements 123a, 123b, and the fifth vibration displacement difference measured between the fifth pair of vibration measurement elements 125a, 125b.

TABLE 1

| Vibration displacement | First vibration measurement element | Second vibration measurement element | Third vibration measurement element | Fourth vibration measurement element | Fifth vibration measurement element |
|---|---|---|---|---|---|
| First side | 60 μm | 30 μm | 10 μm | −25 μm | −40 μm |
| Second side | 50 μm | 20 μm | 6 μm | −35 μm | −50 μm |

TABLE 2

| | First pair of vibration measurement elements | Third pair of vibration measurement elements | Fifth pair of vibration measurement elements |
|---|---|---|---|
| Vibration displacement difference | 10 μm | 4 μm | 10 μm |

In this embodiment, the step of correcting the vibration displacements measured by the first to the fifth vibration measurement elements of either of the first side and second side further includes the following step: comparing the vibration displacements measured by the first, third, and fifth vibration measurement elements on a same side, so as to obtain a minimum vibration displacement, which is regarded as a minimum vibration amplitude, wherein a position of one of the first, third, and fifth vibration measurement elements that corresponds to the minimum vibration displacement is regarded as a closest node, and one of the first, third, and fifth vibration displacement differences that corresponds to the minimum vibration displacement is regarded to be a closest interference value generated by the ambient noise. For example, further refer to Table 1, vibration displacements measured by the first, the third, and the fifth vibration measurement elements are greater; and using the closest interference value generated by the ambient noise to correct the vibration displacements measured by the first vibration measurement element to the fifth vibration measurement element on the side where the vibration displacements are greater. For example, further refer to Table 1, the vibration displacements measured by the first, the third, and the fifth vibration measurement elements 121a, 123a, 125a of the first side 120a are compared with the vibration displacements measured by the first, the third and the fifth vibration measurement elements 121b, 123b, 125b of the second side 120b, to obtain that the first side 120a is a side where the vibration displacements measured by the first, the third, and the fifth vibration measurement elements 121a, 123a, 125a are all greater; and the third vibration displacement difference corresponding to the minimum vibration displacement (namely, the closest ambient interference value generated by the noise) is used to correct the vibration displacements measured by the first to the fifth vibration measurement elements 121a, 122a, 123a, 124a, 125 of the first side 120a. Further refer to Table 3, which shows the corrected vibration displacements of the first side 120a and the uncorrected vibration displacements of the second side 120b.

TABLE 3

| Vibration displacement | First vibration measurement element | Second vibration measurement element | Third vibration measurement element | Fourth vibration measurement element | Fifth vibration measurement element |
|---|---|---|---|---|---|
| First side (Corrected) | 56 μm | 26 μm | 6 μm | −29 μm | −44 μm |
| Second side (Uncorrected) | 50 μm | 20 μm | 6 μm | −35 μm | −50 μm | ments measured by two the third vibration measurement elements 123a, 123b are minimum vibration displacements, which are respectively 10 μm and 6 μm and may be regarded as minimum vibration amplitudes of the first side 120a and second side 120b, and their corresponding positions may be regarded as the closest nodes. In this way, one of the first, third, and fifth vibration displacement differences that corresponds to the minimum vibration displacement (namely, the third vibration displacement difference in this embodiment) is regarded to be an interference value generated by the ambient noise, as shown in Table 2.

Figure 3:
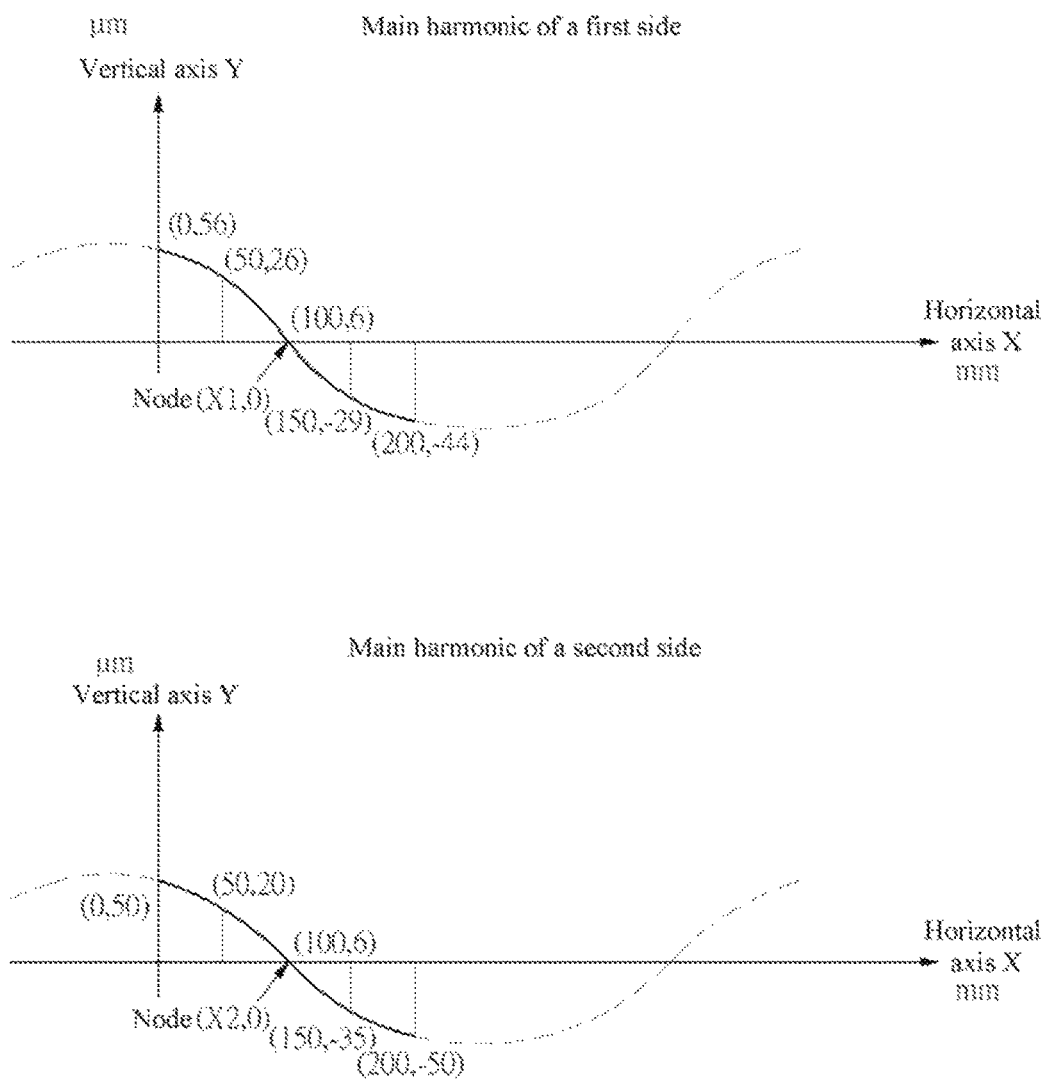
FIG. 3 is a schematic diagram of a pair of main harmonics on the first side and second side during machining according to an embodiment of the present disclosure.

In this embodiment, the step of correcting the vibration displacements measured by the first to the fifth vibration measurement elements of either of the first side and second side further includes the following steps: comparing the vibration displacements measured by the first, the third, and the fifth vibration measurement elements on the first side with the vibration displacements measured by the first, the third, and the fifth vibration measurement elements on the second side, so as to obtain a side where the vibration Step S240: Perform interpolation calculation on the corrected and uncorrected vibration displacements of the first pair of vibration measurement elements, the third pair of vibration measurement elements, and the fifth pair of vibration measurement elements by using the corrected and uncorrected vibration displacements of the second pair and the fourth pair of vibration measurement elements, so as to calculate positions of at least one pair of nodes located on the first side and the second side. For example, refer to Table 4, positions of a pair of nodes that are calculated by using an interpolation method would be located between positions of the third pair of vibration measurement elements 123a, 123b and positions of the fourth pair of vibration measurement elements 124a, 124b, that is, it may be calculated that horizontal axis and vertical axis coordinates of the one pair of nodes are respectively (X1, 0) and (X2, 0), as shown in FIG. 3.

TABLE 4

|  | First vibration measurement element | Second vibration measurement element | Third vibration measurement element | Node | Fourth vibration measurement element | Fifth vibration measurement element |
|---|---|---|---|---|---|---|
| Corrected vibration displacement of first side | 56 μm | 26 μm | 6 μm | 0 | −29 μm | −44 μm |
| Horizontal axis coordinate X | 0 (Assumed) | 50 mm | 100 mm | X1 | 150 mm | 200 mm |
| Vertical axis coordinate Y | 56 μm | 26 μm | 6 μm | 0 | −29 μm | −44 μm |
| Uncorrected vibration displacement of second side | 50 μm | 20 μm | 6 μm | 0 | −35 μm | −50 μm |
| Horizontal axis coordinate X | 0 (Assumed) | 50 mm | 100 mm | X2 | 150 mm | 200 mm |
| Vertical axis coordinate Y | 50 μm | 20 μm | 6 μm | 0 | −35 μm | −50 μm |

Step S250: Use the vibration displacements in steps S220 to S240 to deduce dynamic vibration frequencies of one pair of main harmonics. For example, further refer to Table 4, one pair of main harmonics of the first side 120a and second side 120b during machining may be deduced by using horizontal axis and vertical axis coordinate values of Table 4, as shown in FIG. 3, and dynamic vibration frequencies of the one pair of main harmonics may be deduced.

Step S260: Confirm a vibration mode of the main shaft. For example, a vibration mode of the main shaft 110 may be confirmed by using the dynamic vibration frequencies of the one pair of main harmonics and the positions of the pair of nodes.

In the design of the present disclosure, a dynamic vibration frequency in a cutting process may be quickly measured by using a symmetrical position arranging manner of multiple vibration measurement elements. Because sensed signals of symmetrically arranged positions have the same theoretical value, but are affected by the environment to different extents. Thus, a dynamic vibration frequency, a mode, and a node position during machining may be clearly learned by means of a signal difference calculation manner. The technology of the present disclosure can prevent the precision of the measurement system from being affected by ambient interference, so that the dynamic vibration frequency and the vibration mode during machining may be accurately acquired.

In conclusion, merely implementation manners or embodiments for presenting the technical means used by the present disclosure to resolve technical problems are disclosed, and they are not used to define the scope of implementation of the present disclosure. That is, any equivalent changes or modifications having the meanings consistent with those of the claims of the present disclosure or made according to the claims of the present disclosure are covered by the patent scope of the present disclosure.

What is claimed is:

1. A method for acquiring a dynamic vibration frequency, comprising the following steps of:

selecting five pairs of vibration measurement elements, which comprise a first pair of vibration measurement elements to a fifth pair of vibration measurement elements, wherein the first pair of vibration measurement elements comprises two first vibration measurement elements, the second pair of vibration measurement elements comprises two second vibration measurement elements, and so forth;

determining a bandwidth range of the first pair of vibration measurement elements to the fifth pair of vibration measurement elements;

using the first pair of vibration measurement elements to the fifth pair of vibration measurement elements in sequence on a first side and a second side, which are geometrically symmetrical to each other, of a main shaft to measure vibration displacements in a symmetrical position arranging manner;

correcting the vibration displacements measured by the first vibration measurement element to the fifth vibration measurement element of either of the first side and second side by using a vibration displacement difference measured between the first pair of vibration measurement elements, between the third pair of vibration measurement elements, or between the fifth pair of vibration measurement elements, so as to differentially eliminate an ambient noise;

performing interpolation calculation on the corrected and uncorrected vibration displacements of the first pair of vibration measurement elements, the third pair of vibration measurement elements, and the fifth pair of vibration measurement elements by using the corrected and uncorrected vibration displacements of the second pair of vibration measurement elements and the fourth pair of vibration measurement elements, so as to calculate positions of at least one pair of nodes located on the first side and the second side;

using the vibration displacements in the preceding steps to deduce dynamic vibration frequencies of one pair of main harmonics; and confirming a vibration mode of the main shaft.

2. The method for acquiring a dynamic vibration frequency according to claim 1, wherein the step of correcting the vibration displacements measured by the first vibration measurement element to the fifth vibration measurement element of either of the first side and second side comprises the following step:

calculating a first vibration displacement difference measured between the first pair of vibration measurement elements, a third vibration displacement difference measured between the third pair of vibration measurement elements, and a fifth vibration displacement difference measured between the fifth pair of vibration measurement elements, wherein the first, third, and fifth vibration displacement differences are all regarded as interference values generated by at least one ambient noise.

3. The method for acquiring a dynamic vibration frequency according to claim 2, wherein the step of correcting the vibration displacements measured by the first vibration measurement element to the fifth vibration measurement element of either of the first side and second side further comprises the following step:

comparing the vibration displacements measured by the first, third, and fifth vibration measurement elements on a same side, so as to obtain a minimum vibration displacement, which is regarded as a minimum vibration amplitude, wherein a position of one of the first, third, and fifth vibration measurement elements that corresponds to the minimum vibration displacement is regarded as a closest node, and one of the first, third, and fifth vibration displacement differences that corresponds to the minimum vibration displacement is regarded to be a closest interference value generated by the ambient noise.

4. The method for acquiring a dynamic vibration frequency according to claim 3, wherein the step of correcting the vibration displacements measured by the first vibration measurement element to the fifth vibration measurement element of either of the first side and second side further comprises the following steps:

comparing the vibration displacements measured by the first, the third, and the fifth vibration measurement elements on the first side with the vibration displacements measured by the first, the third, and the fifth vibration measurement elements on the second side, so as to obtain a side where the vibration displacements measured by the first, the third, and the fifth vibration measurement elements are greater; and using the closest interference value generated by the ambient noise to correct the vibration displacements measured by the first vibration measurement element to the fifth vibration measurement element on the side where the vibration displacements are greater.

5. The method for acquiring a dynamic vibration frequency according to claim 1, wherein the main shaft is a main shaft of a cutting machine tool.

6. The method for acquiring a dynamic vibration frequency according to claim 5, wherein the cutting machine tool further comprises a cutting tool, a fixture jig, and a machine tool platform, the cutting tool is fixedly disposed on the main shaft and is configured to cut a workpiece in a rotating manner, the fixture jig is configured to clamp the workpiece, and the machine tool platform is configured to support and hold the fixture jig.

7. The method for acquiring a dynamic vibration frequency according to claim 1, wherein each vibration measurement element is a vibration accelerometer, configured to measure a vibration displacement.

8. The method for acquiring a dynamic vibration frequency according to claim 1, wherein two adjacent vibration measurement elements of the first vibration measurement element to fifth vibration measurement element on the same side are distributed on the main shaft and spaced equally along the main shaft.

9. The method for acquiring a dynamic vibration frequency according to claim 1, wherein two adjacent vibration measurement elements of the first vibration measurement element to fifth vibration measurement element on the same side are distributed on the main shaft and spaced unequally along the main shaft.

* * * * *